US00PP28441P3

(12) United States Plant Patent
Bradford et al.

(10) Patent No.: US PP28,441 P3
(45) Date of Patent: Sep. 26, 2017

(54) PLUM TREE NAMED 'BLACKRED XXI'

(50) Latin Name: *Prunus salicina*
Varietal Denomination: Blackred XXI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 34 days.

(21) Appl. No.: 14/757,268

(22) Filed: Dec. 11, 2015

(65) Prior Publication Data

US 2017/0172029 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP20,892 P2 3/2010 Bradford

*Primary Examiner* — Keith Robinson

(57) ABSTRACT

The present invention relates to a plum tree and more particularly to a new and distinct variety broadly characterized by a large size, vigorous, hardy, and very productive tree. Being self-unfruitful, the present variety requires cross pollination from an apricot, plum, or interspecific variety that blooms during the mid to late season, such as 'September Yummy' plum (U.S. Plant Pat. No. 14,220). The present variety's abundance of blossoms and pollen entices strong bee activity to facilitate pollination. The fruit matures under the ecological conditions described in mid August, with first picking on Aug. 12, 2015, and can hang firm on the tree for up to thirty days. The fruit is medium to large in size, almost entirely black in skin color, clingstone in type, somewhat oblate in shape, red and yellow in flesh color, juicy, very sweet, and excellent in flavor.

1 Drawing Sheet

Botanical classification: *Prunus salicina.*
Varietal denomination: 'BLACKRED XXI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits. The present invention relates to a new and distinct variety of plum tree which has been denominated varietally as 'Blackred XXI'.

During a typical blooming season we isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2003 one such house containing an unpatented purple plum, code named '42P1156', was crossed by us in this manner. To pollinate this purple plum, we selected bouquets from several sources of plum trees without keeping specific written details. Upon reaching maturity the fruit from this plum tree was harvested, and the seeds were removed, cracked, stratified and germinated as a group with the label "H12". They were grown as seedlings on their own root in our greenhouse and upon reaching dormancy transplanted to a cultivated area of our experimental orchard located near Le Grand, Calif. in Merced County (San Joaquin Valley). During the summer of 2007 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was true to type.

The present variety is similar to its seed parent, '42P1156' (unpatented) plum tree, by being self-unfruitful and by producing fruit that is purple to black in skin color, firm in texture, and globose in shape, but is distinguished therefrom by producing fruit that is pink to red instead of yellow in flesh color, that is much sweeter in flavor, and that matures about forty-five days later.

The present variety is most similar to 'Blackred XII' (U.S. Plant Pat. No. 20,892) interspecific tree by being self-unfruitful and by producing fruit that is mostly black in skin color, red and yellow in flesh color, and sweet in flavor, but is distinguished therefrom by blooming about 5 days earlier and by producing fruit that is juicier, that is crisp and melting instead of tough and meaty in texture, that is more heat resistant, and that ripens about fifteen days earlier.

SUMMARY OF VARIETY

The present plum variety is characterized by a large size, vigorous, hardy, and very productive tree. Being self-unfruitful, the present variety requires cross pollination from an apricot, plum, or interspecific variety that blooms during the mid to late season, such as 'September Yummy' plum (U.S. Plant Pat. No. 14,220). The present variety's abundance of blossoms and pollen entices strong bee activity to facilitate pollination. The fruit matures under the ecological conditions described in mid August, with first picking on Aug. 12, 2015, and can hang firm on the tree for up to thirty days. The fruit is medium to large in size, almost entirely black in skin color, clingstone in type, somewhat oblate in shape, red and yellow in flesh color, juicy, very sweet, and excellent in flavor.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Aug. 17, 2015, on the original tree during its twelfth growing season. The flower and bud descriptions were developed during the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: '42P1156' plum (unpatented).
Pollen parent: Unknown.

TREE

Size: Large, reaching a height of 12' [3.66 m.] and a spread of 8' [2.44 m.] after twelve growing seasons utilizing typical pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming apricot, interspecific, or plum, such as such as 'September Yummy' plum tree (U.S. Plant Pat. No. 14,220).

Bearing: Regular bearer, weather dependent, no crop failures observed as of yet.

Trunk:

*Size.*—Medium size, reaching a maximum diameter of 5½" [140 mm.] after the twelfth growing season.

*Texture.*—Medium roughness.

*Bark color.*—A Grayish brown [61. gy.Br] and Light grayish brown [60. l.gy.Br] variegation with Moderate orange [53. m.O] crevices present.

*Lenticels.*—Approximate Number Per Square Inch: 4. Color: Light yellowish brown [76. l.yBr]. Average Size: 5/16" [7.9 mm.] in length. The width is typically one fourth as much as the length. Shape: Eye-shaped.

Branches:

*Size.*—Medium, diameter of main scaffold is 3½" [89 mm.]. measured 12" above the crotch, diameter of secondary limb is 2⅛" [54 mm.] measured 12" above the first fork.

*Texture.*—Fairly smooth on first and second year wood, increasing roughness with age.

*Color.*—1st Year Wood Topside: Grayish red [19. gy.R]. 1st Year Wood Underside: Brilliant yellow green [116. brill.YG]. 2nd Year Wood: A Strong brown [55. s.Br] with Strong yellow green [117. s.YG] permeating through. Older Wood: A Moderate brown [58. m.Br] and Dark orange yellow [72. d.OY] variegation.

*Lenticels.*—Number Per Square Inch: About 20 on second year wood. Color: Light yellowish brown [76. l.yBr]. Average Size: Small, 1/64" [0.4 mm.] in length. The width is typically one fourth as much as the length. Shape: Eye-shaped.

Leaves:

*Size.*—Medium. Average Length: 3 11/16" [93.7 mm.]. Average Width: 1 9/16" [39.7 mm.].

*Arrangement.*—Alternate.

*Thickness.*—Medium.

*Form.*—Elliptical.

*Apex.*—Acuminate.

*Base.*—Acute with an average base angle of 50 degrees.

*Surface.*—Smooth on both sides.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Pale greenish yellow [104. p.gY].

*Petiole.*—Average Length: ⅜" [9.5 mm.]. Average Thickness: 1/16" [1.6 mm.]. Color: Topside is Grayish reddish orange [39. gy.rO] and the underside is Pale greenish yellow [104. p.gY].

*Stipules.*—Number: Usually 2 per leaf, up to 6 per growing tip. Average Length: ¼" [6.4 mm.]. Color: Moderate greenish yellow [102. m.gY] becoming Light grayish reddish brown [45. l.gy.rBr] with age.

*Glands.*—Number: Mostly 2 to 4 per leaf. Position: Alternately positioned at the intersection of the petiole and the leaf blade. Form: Globose. Size: Small, 1/64" [0.4 mm.] in diameter. Color: Moderate yellow green [120. m.YG] acquiring a Dark brown [59. d.Br] center with age.

*Leaf buds.*—Pointed.

Flower buds:

*Hardiness.*—Hardy, with respect to central California blooming season.

*Diameter.*—Typically 3/16" [4.8 mm.] 1 week before bloom.
*Length.*—Typically 3/8" [9.5 mm.] 1 week before bloom.
*Form.*—Not appressed.
*Surface.*—Slightly pubescent.
*Tip color.*—White [263. White].

Flowers: Perfect, complete, perigynous, usually a single pistil, about thirty stamens, five sepals and petal locations alternately positioned.
*Average flower diameter.*—1 1/16" [27.0 mm.].
*Average flower depth.*—3/8" [9.5 mm.] when fully open.
*Average pedicel length.*—3/8" [9.5 mm.].
*Number of petals.*—Five, no double blossoms observed.
*Petal shape.*—Oval to circular.
*Petal margin.*—Entire, smooth to slightly wavy.
*Average petal diameter.*—1/2" [12.7 mm.].
*Average petal length.*—9/16" [14.3 mm.].
*Petal apex.*—Rounded.
*Petal base.*—Obtuse.
*Petal color.*—White [263. White] on both sides.
*Anther color.*—Vivid yellow [82. v.Y].
*Pollen production.*—Abundant, bee enticing.
*Pollen color.*—Strong yellow [84. s.Y].
*Stigma color.*—Brilliant greenish yellow [98. brill.gY].
*Stigma position.*—Located slightly above the surrounding anthers.
*Sepal color.*—Brilliant yellow green [116. brill.YG] with Grayish pink [8. gy.Pk] areas toward the edges on the outer surface. Light yellow green [119. l.YG] on the inner surface.
*Sepal length.*—5/32" [4.0 mm.].
*Sepal width.*—11/64" [4.4 mm.].
*Sepal apex.*—Rounded to elliptical to match the width and length.
*Sepal margin.*—Fairly smooth, with slight serration toward the apex.
*Average pistil length.*—3/4" [19.1 mm.].
*Average stamen length.*—1/2" [12.7 mm.].
*Ovary.*—Smooth.
*Fragrance.*—Moderate.
*Blooming period.*—Medium to late compared to other varieties, three days after 'Santa Rosa' plum (unpatented).
*Onset of bloom.*—One percent on Feb. 21, 2015.
*Date of full bloom.*—Mar. 2, 2015.
*Duration of bloom.*—One to two weeks, dependent on ambient temperature.
*Bloom density.*—Very heavy.
*Number per cluster.*—2 to 9, average 3.

FRUIT

Maturity when described: Firm ripe, Aug. 17, 2015.
Date of first picking: Aug. 12, 2015.
Date of last picking: Sep. 2, 2015.
Size: Mostly uniform, medium to large.
*Average diameter axially.*—2 5/16" [58.7 mm.].
*Average diameter across cheek plane.*—2 9/16" [65.1 mm.].
*Average diameter across suture plane.*—2 11/16" [68.3 mm.].
*Typical weight.*—5.7 ounces [162 grams].
Form: Uniform, symmetrical, moderately oblate, slightly compressed axially.
*Longitudinal section form.*—Oblate.
*Transverse section through diameter.*—Round.
Suture: A shallow groove extending from the base to the apex with a slight depression just beyond the pistil point.
Ventral surface: Rounded, lipped slightly on both sides.
Lips: Slightly unequal.
Cavity: Flaring, slightly elongated in the suture plane with Deep reddish orange [36. deep rO] stem markings present occasionally.
*Depth.*—1/2" [12.7 mm.].
*Breadth.*—1 1/16" [27.0 mm.].
Base: Truncate, slightly cordate if viewed parallel to the suture.
Apex: Rounded, slightly mammiform.
Pistil point: An inconspicuous Pale yellow [89. p.Y] dot located at the end of the suture.
Stem: Small to medium.
*Average length.*—7/16" [11.1 mm.].
*Average width.*—1/8" [3.2 mm.].
Skin:
*Thickness.*—Medium.
*Surface.*—Smooth.
*Tenacity.*—Tenacious to the flesh.
*Astringency.*—Moderate.
*Tendency to crack.*—None observed.
*Color.*—Blackish red [21. blackish R] smoothly blending into a Very dark red [17. v.d.R] background with heavy Light yellow [86. l.Y] freckling throughout.
*Lenticels.*—Number Per Square Inch: About 80 toward the apex. Average diameter: 1/48" [0.5 mm].
*Bloom.*—Moderate to heavy.
Flesh:
*Color.*—Moderate red [15. m.R] toward the skin, Light yellow [86. l.Y] in the middle, and Pale yellowish pink [31. p.yPk] toward the stone.
*Surface of pit cavity.*—Covered with Vivid red [11. v.R] broken fibers when twisted away from stone.
*Amygdalin.*—Moderate.
*Juice.*—Abundant, rich.
*Texture.*—Firm, crisp, melting, can hang firm on the tree for up to thirty days.
*Fibers.*—Abundant, fine, tender.
*Ripens.*—Fairly even.
*Flavor.*—A tasty balance of acid and sugar, typically 22 to 24 brix.
*Aroma.*—Slight.
*Eating quality.*—Excellent.

STONE

Type: Clingstone.
Form: Oval.
Hilum: Narrow, oblong.
Base: Rounded to cordate.
Apex: Acuminate.
Sides: Equal.
Surface: Rough, some irregular furrows and ridges mostly near the base.
External color of stone: Dark orange yellow [72. d.OY] with exposure.
Pit wall color when cracked: Pale orange yellow [73. p.OY].
Cavity surface color: Light orange yellow [70. l.OY].
Average pit wall thickness: 1/8" [3.2 mm.].

Average length: 1" [25.4 mm.].
Average width: ¾" [19.1 mm.].
Average breadth: 7/16" [11.1 mm.].
Tendency to split: None observed.
Kernel:
*Form.*—Oval.
*Skin color.*—Light yellowish brown [76. l.yBr].
*Pellicle color.*—Dark yellowish brown [78. d.yBr].
*Vein color.*—Deep yellowish brown [75. deep yBr].
*Taste.*—Bitter.
*Viable.*—Yes.
*Average width.*—⅜" [9.5 mm.].
*Average length.*—9/16" [14.3 mm.].
*Amygdalin.*—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described that is most similar to 'Blackred XII' (U.S. Plant Pat. No. 20,892) interspecific tree by being self-unfruitful and by producing fruit that is mostly black in skin color, red and yellow in flesh color, and sweet in flavor, but is distinguished therefrom by blooming about 5 days earlier and by producing fruit that is juicier, that is crisp and melting instead of tough and meaty in texture, that is more heat resistant, and that ripens about fifteen days earlier.

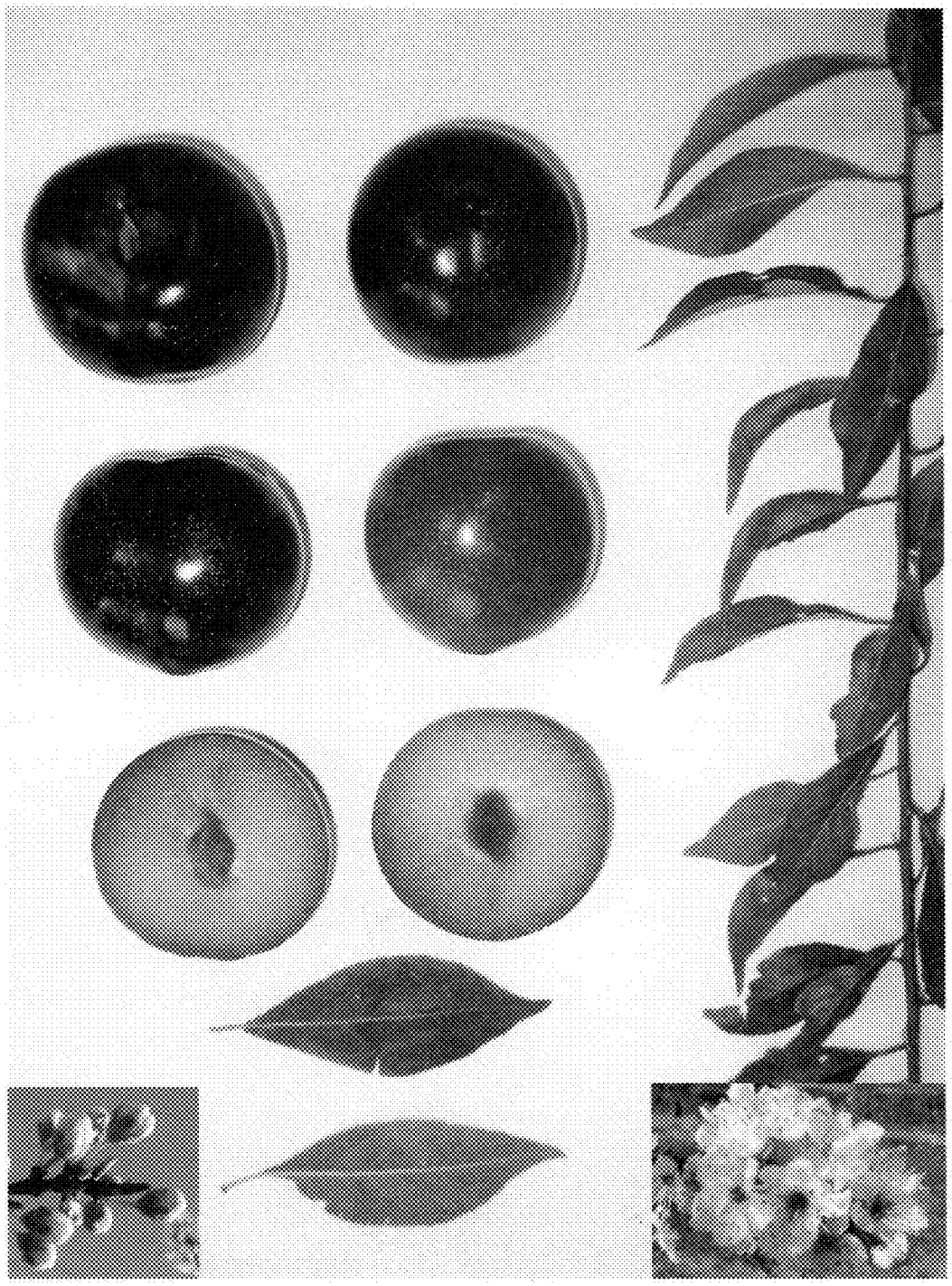

* * * * *